United States Patent [19]

Jefson et al.

[11] Patent Number: 4,861,779
[45] Date of Patent: Aug. 29, 1989

[54] ANTI-BACTERIAL SUBSTITUTED BRIDGED-DIAZABICYCLOALKYL QUINOLONE CARBOXYLIC ACIDS

[75] Inventors: Martin R. Jefson, Oakdale; Paul R. McGuirk, Gales Ferry, both of Conn.

[73] Assignee: Pfizer Inc., New York, N.Y.

[21] Appl. No.: 898,473

[22] Filed: Aug. 19, 1986

Related U.S. Application Data

[63] Continuation-in-part of Ser. No. 777,471, Sep. 18, 1985, abandoned.

[51] Int. Cl.⁴ .................. A61K 31/495; A61K 31/44; C07D 471/08; C07D 487/08
[52] U.S. Cl. ..................................... 514/249; 514/312; 540/472; 540/556; 544/282; 546/123; 546/156
[58] Field of Search ............... 546/123, 156; 544/349; 514/249, 312

[56] References Cited

U.S. PATENT DOCUMENTS

| 4,146,719 | 3/1979 | Irikura | 544/363 |
| 4,292,317 | 9/1981 | Pesson | 546/156 X |
| 4,382,892 | 5/1983 | Hayakawa et al. | 544/101 |
| 4,448,962 | 5/1984 | Irikura et al. | 546/156 X |
| 4,499,091 | 2/1985 | Wentland et al. | 546/156 |
| 4,571,396 | 2/1986 | Hutt et al. | 546/123 |

FOREIGN PATENT DOCUMENTS

| 107300 | 9/1983 | Australia . | |
| 131839 | 1/1985 | European Pat. Off. | 546/156 |
| 112876 | 9/1979 | Japan | 546/156 |
| 204193 | 5/1983 | Japan . | |
| 204194 | 5/1983 | Japan . | |
| 219293 | 5/1983 | Japan . | |
| 023381 | 7/1983 | Japan . | |
| 023382 | 7/1983 | Japan . | |
| 137481 | 8/1984 | Japan . | |

OTHER PUBLICATIONS

Amacher et al., Mutation Research vol. 64, p. 391–406 (1979).
Amacher et al., Mutation Research, vol. 72, p. 447–474, (1980).
Amacher et al., Mutation Research vol. 97, p. 49–65, (1982).
Heidelberger, Cancer Research, vol. 30(6), p. 1549–1565.
Clive et al., Mutation Research, vol. 31, p. 17–29 (1973).
Domagala et al., J. Med. Chem. vol. 29, p. 394–404, (1986).
Barrett et al., 27th Interscience Conference on Anti-Microbial Agents And Chemotherapy, p. 249–252 (1987).

Primary Examiner—Mary C. Lee
Assistant Examiner—Bernard I. Dentz
Attorney, Agent, or Firm—Peter C. Richardson; Paul H. Ginsburg; Gezina Holtrust

[57] ABSTRACT

Antibacterial compounds have the formula

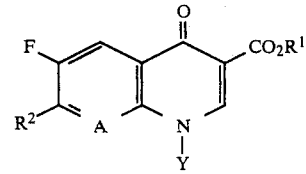

wherein $R^1$ is hydrogen, a pharmaceutically acceptable cation, or alkyl; A is CH, CF, CCl or N; Y is alkyl, haloalkyl, cyclopropyl, vinyl, methoxy, N-methylamino, p-fluorophenyl, p-hydroxyphenyl or p-aminophenyl; or A is carbon and is taken together with Y and the carbon and nitrogen to which A and Y are attached to form a five to seven membered ring which is optionally substituted; and $R^2$ is a bridged-diazabicycloalkyl group.

15 Claims, No Drawings

ANTI-BACTERIAL SUBSTITUTED BRIDGED-DIAZABICYCLOALKYL QUINOLONE CARBOXYLIC ACIDS

CROSS-REFERENCE TO RELATED APPLICATION

This is a continuation in part of application Ser. No. 777,471 filed Sept 18, 1985, abandoned.

BACKGROUND OF THE INVENTION

This invention relates to substituted bridged-diazabicycloalkyl quinolone carboxylic acids and acid derivatives thereof, antibacterial compositions containing said compounds, and a method of using said compounds.

Since the introduction of nalidixic acid, 1,4-dihydro-1-ethyl-4-oxo-7-methyl-1,8-naphthyridine-3carboxyl acid, in 1963, a considerable number of patents and scientific papers have been published on compounds having a related structure.

For instance, Australian Patent No. 107300 discloses compounds of the formula

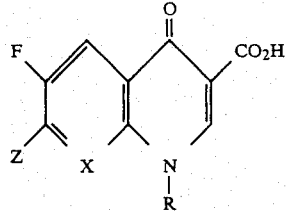

wherein X may be CF or CH, R may be lower alkyl and Z may be a heterocyclic group such as 1-pyrrolidinyl or a spiro group such as 2,7-diazaspiro[4,4]non-2-yl.

Japanese Patent No. 056219 discloses norfloxacin, 1-ethyl-6-fluoro-1,4-dihydro-7-piperazino-4-oxo-quinoline-3-carboxylic acid, European patent publication 78362 discloses ciprofloxacin, 1-cyclopropyl-1,4-dihydro-4-oxo-6-fluoro-7-piperazinoquinoline-3-carboxylic acid, and European patent publication 47005 discloses similar piperazinoquinolines wherein a third ring connects the positions 1 and 8 of the quinolone group. Diazabicycloalkane hydroquinoline and benzoxazine carboxylic acids are disclosed in Japanese Patent Publications 59219293, 59204194, 59204195, 59137481, 60023381 and 60023382.

The above references all disclose antibacterial activity for their compounds.

SUMMARY OF THE INVENTION

In accordance with the invention, antibacterial compounds are provided having the formula I:

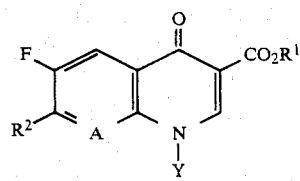

or a pharmaceutically acceptable acid addition salt thereof, wherein $R^1$ is hydrogen, a pharmaceutically acceptable cation, or $(C_1-C_6)$alkyl;

A is CH, CF, CCl or N;

Y is $(C_1-C_3)$alkyl, $(C_1-C_3)$haloalkyl, cyclopropyl, vinyl, methoxy, N-methylamino, p-fluorophenyl, p-hydroxyphenyl or p-aminophenyl; or A is carbon and is taken together with Y and the carbon and nitrogen to which A and Y are attached to form a five or six membered ring which may contain O, and which may have attached thereto R' which is methyl or methylene; and $R^2$ is a bridged-diazabicycloalkyl substituent selected from the group consisting of

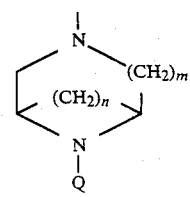
a

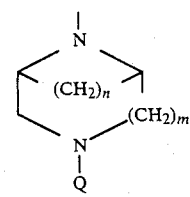
b

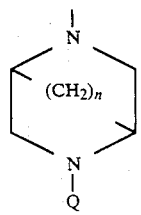
c

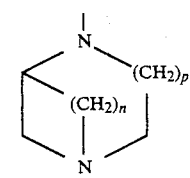
d

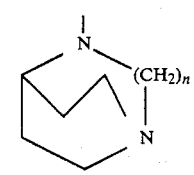
e wherein
n is 1, 2 or 3;
m is 1 or 2;
p is 0 or 1; and
Q is hydrogen, $(C_1-C_3)$alkyl, $(C_1-C_6)$alkyl-carbonyl or $(C_1-C_6)$alkoxy carbamoyl.

The compounds of the invention include tricyclic compounds wherein A is carbon and A and Y are taken together with the carbon and nitrogen to which they are respectively attached to form a five or six membered ring which may contain oxygen. The oxygen may be present at any available position in the ring but is preferably attached to A. The tricyclic compounds of formula I wherein R' is methylene preferably have the methylene group on the carbon attached to the quinoline nitrogen atom. Preferably, compounds (I) wherein A and Y are taken together have the formula:

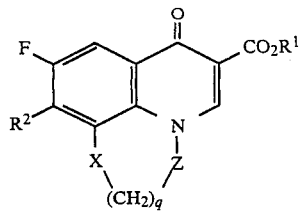

wherein X is CH₂ or O, q is 0 or 1 and Z is CH₂, CH(CH₃) or C=CH₂.

Preferred compounds of the invention are those of formula I wherein $R^1$ is hydrogen or a pharmaceutically acceptable cation such as sodium or potassium.

Other preferred compounds (I) are those wherein Y is ethyl.

Specific preferred compounds are as follows:
1-ethyl-6-fluoro-1,4-dihydro-7-(8-methyl-3,8-diazabicyclo[3.2.1]oct-3-yl)-4-oxo-3-quinoline carboxylic acid,
1-ethyl-6-fluoro-1,4-dihydro-7-(1,4-diazabicyclo[3.2.2.]-non-4-yl)-4-oxo-3-quinoline carboxylic acid,
1-vinyl-6-fluoro-1,4-dihydro-7-(8-methyl-3,8-diazabicyclo[3.2.1]oct-3-yl)-4-oxo-3-quinoline carboxylic acid,
1-vinyl-6-fluoro-1,4-dihydro-7-(1,4-diazabicyclo[3.2.2.]-non-4-oxo-3-quinoline carboxylic acid,
10-(1,4-diazabicyclo[3.2.2]non-4-yl)-9-fluoro-3-methyl-7-oxo-2,3-dihydro(7H)-pyrido[1,2,3-de]-1,4-benzoxazine-6-carboxylic acid,
1-cyclopropyl-6-fluoro-1,4-dihydro-7-(1,4-diazabicyclo[3.2.2]non-4-yl)-4-oxo-3-quinoline carboxylic acid,
1-(2-fluoroethyl)-6-fluoro-1,4-dihydro-7-(8-methyl-3,8-diazabicyclo[3.2.1]oct-3-yl)-4-oxo-3-quinoline carboxylic acid,
1-cyclopropyl-6-fluoro-1,4-dihydro-7-(2,5-diazabicyclo[2.2.1]hept-2-yl)-4-oxo-3-quinoline carboxylic acid,
1-cyclopropyl-6-fluoro-1,4-dihydro-6-(8-methyl-3,8-diazabicyclo[3.2.1]oct-3-yl)-4-oxo-3-quinoline carboxylic acid,
1-ethyl-6,8-difluoro-1,4-dihydro-7-(1,4-diazabicyclo[3.2.2]non-4-yl)-4-oxo-3-quinoline carboxylic acid,
1-(4-fluorophenyl)-6-fluoro-1,4-dihydro-7-(1,4diazabicyclo[3.2.2]non-4-yl)-4-oxo-3-quinoline carboxylic acid,
1-methylamino-6-fluoro-1,4-dihydro-7-(1,4-diazabicyclo[3.2.2]non-4-yl)-4-oxo-3-quinoline carboxylic acid,
1-(2-fluoroethyl)-6,8-difluoro-1,4-dihydro-7-(1,4-diazabicyclo[3.2.2]non-4-yl)-4-oxo-3-quinoline carboxylic acid, and
1-ethyl-6-fluoro-1,4-dihydro-7-(2,5-diazabicyclo[2.2.1]hept-2-yl)-4-oxo-3-quinoline carboxylic acid.

In one embodiment, the compounds of the invention have the following formula:

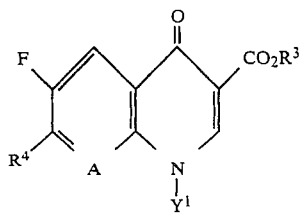

or a pharmaceutically acceptable acid addtion salt thereof, wherein
$R^3$ is hydrogen, a pharmaceutically acceptable cation, or $(C_1-C_6)$alkyl;
A is CH, CF, CCl or N;
$Y^1$ is methoxy, N-methylamino, p-fluorophenyl, p-hydroxyphenyl or p-aminophenyl; or
A is carbon and is taken together with Y and the carbon and nitrogen to which A and Y are attached to form a six membered ring which may contain oxygen, and which may have attached thereto R' which is methyl or methylene, and
$R^4$ is a bridged-diazabicycloalkyl substituent selected from the group consisting of

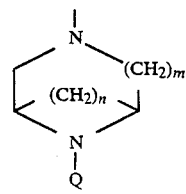

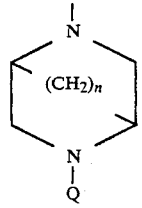

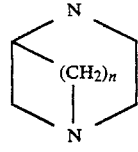

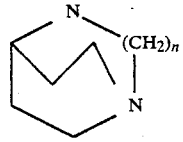

wherein
m is 1 of 2;
n is 2 or 3; and
Q is hydrogen, $(C_1-C_3)$alkyl, $(C_1-C_6)$alkoxy-carbonyl or $(C_1-C_6)$alkyl-carbamoyl.

Preferred compounds within this embodiment have the formula IA wherein $R^3$ is hydrogen, A is CH, CF, or N, and $Y^1$ is methoxy, N-methylamino, p-fluorophenyl, p-hydroxyphenyl or p-amininophenyl.

Other preferred compounds have the formula

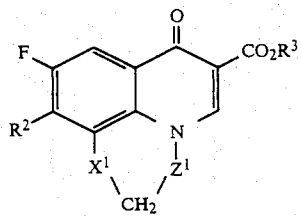

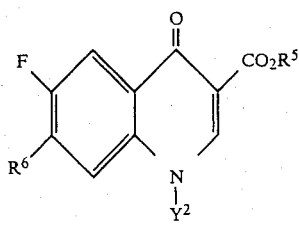

wherein $X^1$ is $CH_2$ or O, and $Z^1$ is $CH_2$, or $C=CH_2$.

The above two preferred classes of compounds may have a group $R^4$ which is selected from 8-methyl-3,8-diazabicyclo[3.2.1]oct-3-yl; 1,4-diazabicyclo[3.2.2]non-4-yl; 9-methyl-3,9-diazabicyclo[4.2.1]non-3-yl; 3,9-diazabicyclo[4.2.1]non-3-yl; 2,5-diazabicyclo[2.2.1]hept-2-yl; 9-methyl-3-,9-diazabicyclo[3.3.1]-non-3-yl; 2,5-diazabicyclo[2.2.1]hept-2-yl; 5-methyl-2,5-diazabicyclo[2.2.1]hept-2-yl; 1,4-diazabicyclo[3.3.1]-non-4-yl; 5-methyl-2,5-diazabicyclo[2.2.2]oct-2-yl; and 2,5-diazabicyclo[2.2.2]oct-2-yl.

Specific preferred compounds are 1-methoxy-6-fluoro-7-(8-methyl-3,8-diazabicyclo[3.2.1]oct-3-yl)-1,4-dihydro-4-oxo-3-quinoline carboxylic acid, 1-methoxy-6-fluoro-7-(1,4-diazabicyclo[3.2.2]non-4-yl)-1,4-dihydro-4-oxo-3-quinolone carboxylic acid, 1-methoxy-6-fluoro-7-(2,5-diazabicyclo[2.2.1]hept-2-yl-1,4-dihydro-4-oxo-3-quinoline carboxylic acid, 1-methoxy-6-fluoro-7-(5-methyl-2,5-diazabicyclo[2.2.1]-hept-2-yl)-1,4-dihydro-4-oxo-3-quinoline carboxylic acid, 1-methoxy-6-fluoro-7-(1,4-diazabicyclo[3.3.1]-non-4-yl)-1,4-dihydro-4-oxo-3-quinoline carboxylic acid, 1-methoxy-6-fluoro-7-(5-methyl-2,5-diazabicyclo[2.2.2]oct-2-yl)-1,4-dihydro-4-oxo-3-quinoline carboxylic acid, 1-methoxy-6-fluoro-7-(2,5-diazabicyclo[2.2.2]oct-2-yl)-1,4-dihydro-4-oxo-3-quinoline carboxylic acid, 1-(p-fluorophenyl)-6-fluoro-7-(1,4-diazabicyclo[3.3.2]non-4-yl)-1,4-dihydro-4-oxo-3-quinoline carboxylic acid, 1-(p-fluorophenyl)-6-fluoro-7-(5-methyl-2,5-diazabicyclo[2.2.1]hept-2-yl)-1,4-dihydro-4-oxo-3-quinoline carboxylic acid, 1-(p-fluorophenyl)-6-fluoro-7-(1,4-diazabicyclo[3.3.1]non-4-yl)-1,4-dihydro-4-oxo-3-quinoline carboxylic acid, 1-(p-fluorophenyl)-6-fluoro-7-(5-methyl-2,-5-diazabicyclo[2.2.2]oct-2-yl-1,4-dihydro-4-oxo-3-quinoline carboxylic acid, 1-(p-fluorophenyl)-6-fluoro-7-(2,5-diazabicyclo[2.2.2]oct-2-yl)1,4-dihydro-4-oxo-3-quinoline carobyxlic acid, 1-methylamino-6-fluoro-7(1,4-diazabiyclo[3.2.2]non-4-yl)-1,4-dihydro-4-oxo-3-quinoline carboxylic acid, 1-methylamino-6-fluoro-7(5-methyl-2,5-diazabicyclo[2.2.1]hept-2-yl)-1,4-di-hydro-4-oxo-3-quinoline carboxylic acid, 1-methylamino-6-fluoro-7-(1,4-diazabicyclo[3.3.1]non-4-yl)-1-1,4-dihydro- 4-oxo-3-quinoline carboxylic acid, 1-methylamino-6-fluoro-6-(5-methyl-2,5-diazabicyclo[2.2.2]oct-2-yl)-1,4-dihydro-4-oxo-3-quinoline carboxylic acid, 1-methylamino-fluoro-7-(2,5diazabicyclo[2,2,2]oct-2-yl)-1,4-dihydro-4-oxo-3-quinoline carboxylic acid.

In another embodiment, the compounds of the invention have the formula:

or a pharmaceutically acceptable acid addition salt thereof, wherein $R^5$ is hydrogen, a pharmaceutically acceptable cation, or ($C_1$–$C_6$)alkyl; A is CH, CF, CCl or N; $Y^2$ is ($C_1$–$C_3$)alkyl, ($C_1$–$C_3$)haloalkyl, cyclopropyl or vinyl; or A is carbon and is taken together with $Y^2$ and the carbon and nitrogen to which A and $Y^2$ are attached to form a six-membered ring which may contain oxygen and which may have attached thereto R' which is methyl or methylene; and $R^6$ is a bridged-diazabicycloalkyl substituent selected from the group consisting of 1,4-diazabicyclo[3.2.2]non-4-yl, 1,4-diazabicyclo[3.3.1]non-4-yl, 1,4-diazabicyclo[4.2.2]dec-4-yl,

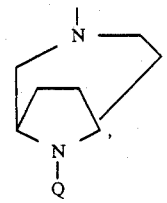

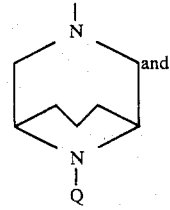

and

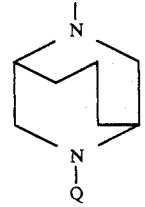

wherein Q is hydrogen, ($C_1$–$C_3$)alkyl, ($C_1$–$C_6$)alkylcarbonyl or ($C_1$–$C_6$-)alkylcarbamoyl. In a specific embodiment, $R^5$ is hydrogen. Specific compounds of formula IB are 1-ethyl-6-fluoro-1,4-dihydro-7-(1,4diazabicyclo[3.2.2]non-4-yl)-4-oxo-3-quinoline-carboxylic acid, 1-ethyl-6-fluoro-1,4-dihydro-7-(1,4diazabicyclo[3.3.1]-non-4-yl)-4-oxo-3-quinoline-carboxylic acid, 1-ethyl-6,8-difluoro-1,4-dihydro-7(1,4-diazabicyclo[3.2.2]non-4-yl)-4-oxo-3-quinoline-carboxylic acid, 1-vinyl-6-fluoro-1,4-dihydro-7(1,4-diazabicyclo[3.3.1.]non-4-yl)-4-oxo-3-quinoline-carboxylic acid, 1-cyclopropyl-6-fluoro-1,4-dihydro-7-(9-methyl-3,9-diazabicyclo[4.2.1]-non-3-yl)-1,4-dihydro-4-oxo-3-quinolinecarboxylic acid, and 10-(1,4diazabicyclo[3.2.2]non-4-yl)-9-fluoro-3-methyl-7-oxo-2,3-dihydro-(7H)-pyrido[1,2,3-de]-1,4-benzoxazine-6-carboxylic acid.

In yet another embodiment, the compounds of the invention have the following formula:

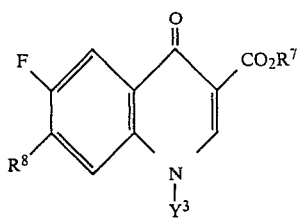

or a pharmaceutically acceptable acid addition salt thereof, wherein $R^7$ is hydrogen, a pharmaceutically acceptable cation, or ($C_1$–$C_6$)alkyl; $Y^3$ is ($C_1$–$C_3$)alkyl or cyclopropyl; and $R^8$ is 3,8-diazabicyclo[3.2.1]oct-3-yl, 8-methyl-3,8-diazabicyclo[3.2.1]oct-3-yl, (1S,4S)-2,5-diazabicyclo[2.2.1]hept-2-yl, (1S,4S)-5-methyl-2,5-diazabicyclo[2.2.1]hept-2-yl, 2,5-diazabicyclo[2.2.2]oct-2-yl, or 5-methyl-2,5diazabicyclo[2.2.2]oct-2-yl. In more specific embodiments, $R^7$ is hydrogen and/or $Y^3$ is ethyl or cyclopropyl. Preferred compounds are 1-ethyl-6-fluoro-1,4-dihydro-7-[(1S,4S)-5-methyl-2,5-diazabicyclo[2.2.1]hept-2-yl]-4-oxo-3-quinoline carboxylic acid, 1-ethyl-6-fluoro-1,4-dihydro-7-(5-methyl-2,5diazabicyclo[2.2.2]oct-2-yl)-4-oxo-3-quinoline carboxylic acid, 1-ethyl-6-fluoro-1,4-dihydro-7-(3,8-diazabicyclo[3.2.1]oct-3-yl)-4-oxo-3-quinoline carboxylic acid, 1-cyclopropyl-6-fluoro-1,4-dihydro-7-(8-methyl-3,8-diazabicyclo[3.2.1]oct-3-yl)-4-oxo-3-quinoline carboxylic acid, 1-cyclopropyl-6-fluoro-1,4-dihydro-7-[(1S,4S)-2,5-diazabicyclo[2.2.1]hept-2-yl]-4-oxo-3-quinoline carboxylic acid, 1-cyclopropyl-6-fluoro-1,4-dihydro-7-[(1S,4S)-5-methyl-2,5-diazabicyclo-[2.2.1]hept-2-yl]-4-oxo-3-quinoline carboxylic acid, 1-cyclopropyl-6-fluoro-1,4-dihydro-7-(2,5-diazabicyclo[2.2.2]oct-2-yl)-4-oxo-3-quinoline carboxylic acid, 1-cyclopropyl-6-fluoro-1,4-dihydro-7-(5-methyl-2,5-diazabicyclo[2.2.2]oct-2-yl)-4-oxo-3-quinoline carboxylic acid, and 1-cyclopropyl-6-fluoro-1,4-dihydro-7-(3,8-diazabicyclo[3.2.1]oct-3-yl)-4-oxo-3-quinoline carboxylic acid.

The compounds of the invention may have chiral centers in view of the bridged structures resulting in formation of stereoisomers. Compounds (I) wherein $R^2$ is c have a chiral center at the carbon atom in the bridge alpha to the nitrogen atom. Compounds (I) wherein $R^2$ is d have a chiral center at the carbon atom which is alpha to the nitrogen atom linking $R^2$ to the quinolone group. These steroisomers may be designated with reference to R and S rotation in accordance with standard nomenclature. The comounds of the invention include racemic mixtures and optical isomers.

The invention includes pharmaceutical compositions comprising a pharmaceutically acceptable carrier or diluent and a compound of the formulae I, IA, IB or IC in an antibacterially effective amount. The pharmaceutical compositions preferably contain the above specific, preferred, and specific preferred compounds.

The invention yet further provides a method of treating an animal, including a human being, having a bacterial disease which comprises administering to the animal an antibacterially effective amount of a compound of the formula I, IA, IB or IC or a pharmaceutical composition as defined above.

DETAILED DESCRIPTION OF THE INVENTION

The compounds (I) of the invention may be prepared by reacting a compound of the formula II:

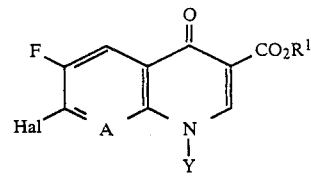

with a compound of the formula $R^2H$ or derivatives thereof wherein $R^1$, $R^2$, A, and Y are as defined above in connection with formula I, and Hal is halogen such as fluoro, chloro or bromo The reaction may be performed with or without a solvent, preferably at elevated temperature, and for a time sufficient to substantially complete the reaction The reaction is preferably carried out in the presence of an acid acceptor such as an inorganic or organic base, e.g. an alkali metal or alkaline earth metal carbonate or bicarbonate or a tertiary amine such as triethylamine, pyridine or picoline.

The solvents for this reaction are solvents which are non-reactive under the reaction conditions such as acetonitrile, tetrahydrofuran, ethanol, chloroform, dimethylsulfoxide (DMSO), dimethylformamide, pyridine, water, or mixtures thereof.

The reaction temperature usually ranges from about 20° C. to about 150° C.

The starting materials of formula II are known in the art, e.g. as disclosed in Australian Patent 107300, and U.S. Pat. Nos. 4,382,892 and 4,416,884.

The starting materials of formula $R^2H$ have the following more specific formulae

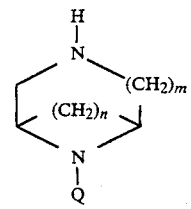

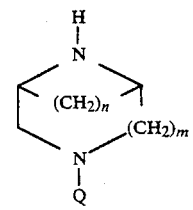

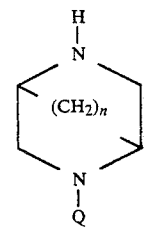

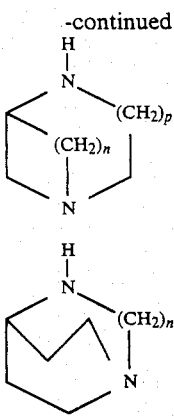

wherein Q, m, n and p are as defined above.

The compounds of formulas III to VII are either known or may be made by methods analogous to those described in the prior art from known starting materials.

Compound (III) wherein m and n are each one and Q is methyl is prepared according to Reaction Scheme I from glutaric acid. First, dibromoglutarate diethylester is formed by treatment of glutaric acid with thionyl chloride, removal of excess reagent, treatment with bromine and quenching with excess ethanol in accordance with the method described in Org. Syn., Coll. Vol. III, 623 (1955). The dibromodiester is reacted with anhydrous methylamine in a sealed autoclave at 90° C. in toluene to give aminoester 3 in accordance with U.S. Pat. No. 3,947,445. Monobenzamide 4 (Ph is phenyl) is obtained by reaction with benzylamine in refluxing xylenes. Cyclization to imide 5 is by heating to 200°–210° C. for about 48 hours. The 7-benzyl derivative of compound III wherein m and n are each one is obtained on reduction with sodium bis(2-methoxyethoxy)aluminum hydride (Red-Al). Catalytic debenzylation with palladium on carbon in acidic methanol affords the desired product Compound (I) wherein $R^2$ is derived from compound (III) wherein n and m are one and Q is hydrogen may be obtained by the sequence described in Reaction Scheme II starting with the dibromodiester 2 of Scheme I.

The diester 2 is reacted with benzylamine (3 equivalents) in refluxing toluene to give N-benzyl-2,4-dicarboethoxy azetidine 7. After catalytic removal of the benzyl group, e.g. with 10% Pd-carbon (Pd/C) catalyst to 8, benzamide 9 is formed on reaction with about one equivalent of benzylamine and cyclized to imide 10 by heating to about 200°–210° C. for about 48 hours. After reduction with Red-Al to compound 11, reaction with ethylchloroformate provides carbamate 12 which is debenzylated by catalytic hydrogenation with 10% Pd-C to 13. Intermediate 13 is reacted with compound (II) wherein $R^1$ is hydrogen and A and Y are as defined above in connection with compounds of formula I. The reaction product is hydrolyzed under standard conditions in aqueous acid or base to remove the ethoxycarbonyl group and provide compound (I) wherein $R^2$ is 3,7-diazabicyclo[3.1.1]-heptyl (III wherein n=m=1 and Q=H).

The compounds (I) wherein $R^2$ is derived from formula IV wherein n and m are 1 and Q is hydrogen or methyl may be prepared by reacting compound 11 of Scheme II in a standard displacement reaction with compound (II) wherein $R^1$ is hydrogen and A and Y are as defined before in connection with compound (I). The formed product is debenzylated by catalytic hydrogenation with e.g. 10% Pd-C to give compound (I) wherein $R_3$ is 3,7-diazabicyclo[3.1.1]heptyl. Reaction with formaldehyde and formic acid provides the corresponding compound (I) wherein Q is methyl.

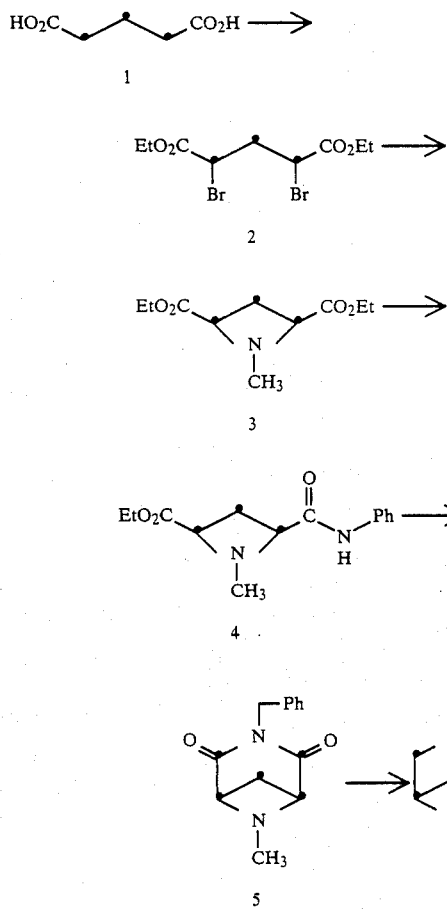

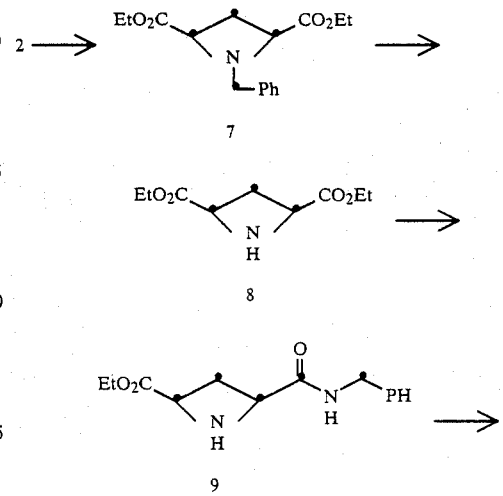

-continued
Reaction Scheme II

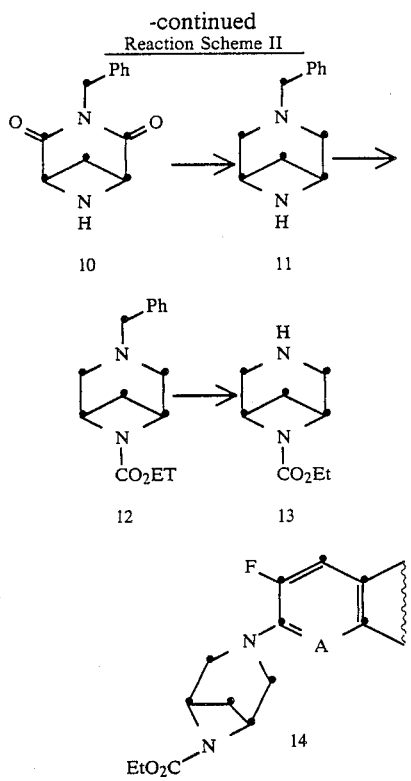

compound (II) wherein $R^1$ is hydrogen and A and Y are as defined before in connection with compound (I). The formed product is debenzylated by catalytic hydrogenation with e.g. 10% Pd-C to give compound (I) wherein $R_3$ is 3,7-diazabicyclo[3.1.1]heptyl. Reaction with formaldehyde and formic acid provides the corresponding compound (I) wherein Q is methyl.

Compounds (III) and (IV) wherein n is 2 and m is 1 are described in U.K. Patent No. 937,183.

Compounds (III) wherein n is 3 and m is 1 are described in J. Amer. Chem. Soc., 75, 975 (1953).

Compound (III) wherein n is 1, m is 2 and Q is methyl,1,8-methyl-3,8-diazabicyclo[4.1.1]octane, may be prepared by the method of Reaction Scheme III by starting with commercially available pimelic acid diethylester 15. The ester 15 is treated with lithium diisopropylamine in tetrahydrofuran to give the dianion which is quenched with about 2 equivalents of phenylselenium chloride. The formed diselenide is oxidized with metachloroperbenzoic acid and heated to form the dienoate 16. A double Michael addition of monoethylamine results in azetidine 17. Ketone 18 is formed by Dieckmann cyclization of 17 with potassium t-butoxide in toluene at reflux temperature. Oxime 19 is formed on reaction with hydroxylamine in aqueous sodium bicarbonate and rearranged with hot sulfuric acid to lactam 20. The desired compound 21 forms on reduction with lithium aluminum hydride (LiAlH4).

Compound (I) wherein $R^2$ is derived from compound (III) wherein n is 1, m is 2 and Q is hydrogen is formed on reacting benzylamine rather than monomethylamine with compound 16 in Scheme III. Proceeding as in Scheme III, 8-benzyl-3,8-diazabicyclo[4.1.1]octane is formed which is coupled with compound (II) and then debenzylated by catalytic hydrogenation, as before.

Compound (IV) wherein n is 1, m is 2 and Q is methyl, 3-methyl-3,8-diazabicyclo[4.1.1]octane, is prepared as in Scheme III reacting 16 with benzylamine instead of monomethylamine and reacting N-benzyl substituted lactam 20 with methyliodide in the presence of sodium hydride and dimethylformamide before reduction of the lactam with lithium aluminum hydride Debenzylation by catalytic hydrogenation provides the desired compound.

Compound (I) wherein $R^2$ is derived from compound (IV) wherein n is 1, m is 2 and Q is hydrogen is prepared by reacting lactam 20 which is N-benzyl substituted as described above with lithium aluminum hydride in tetrahydrofuran (THF). The secondary amino group in the compound is reacted with ethylchloroformate in an inert solvent with pyridine to provide carbamate 22

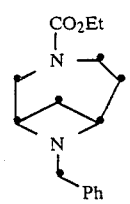

On standard debenzylation, the formed secondary amine is reacted with compound (II) and the resulting intermediate hydrolyzed in aqueous acid or base to give the final product of formula I wherein $R^2$ is derived from compound (IV).

Compound (III) wherein m and n are 2 and Q is methyl is prepared from commercially available tropinone 23 as outlined in Reaction Scheme IV. Tropinone is reacted with hydroxylamine in sodium bicarbonate to form the corresponding oxime which is rearranged with hot sulfuric acid to lactam 24 and reduced with LiAlH4 in THF at reflux temperature to form 25.

Reaction Scheme III

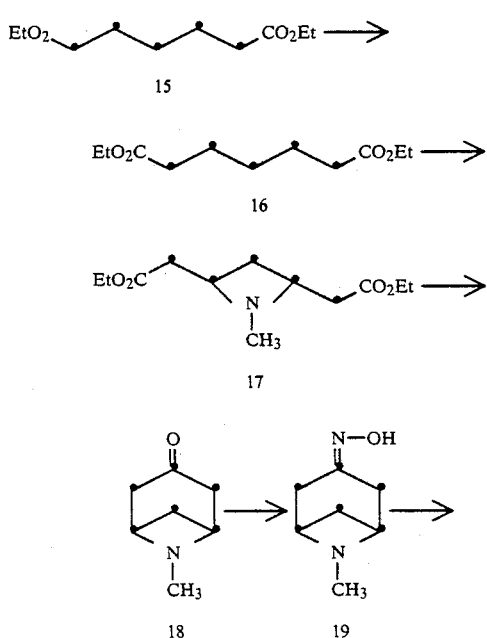

Reaction Scheme III

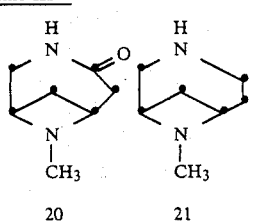

Reaction Scheme V

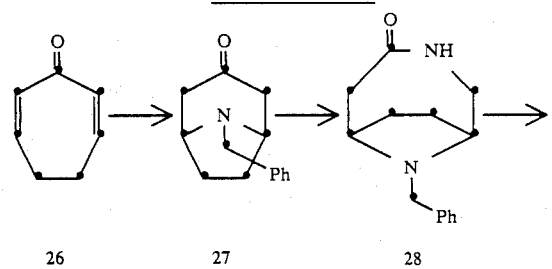

Reaction Scheme IV

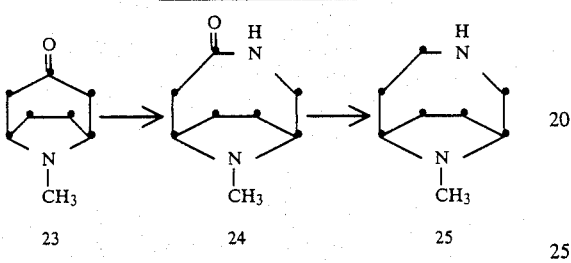

Reaction Scheme V shows the preparation of a derivative of compound (III) wherein m and n are each 2. The known compound 26, 2,6-cycloheptadienone, J. Org. Chem., 44, 4285 (1979), is reacted with benzylamine to form the bridged bicyclic ketone 27. The standard Beckmann rearrangement via the oxime in hot sulfuric acid results in lactam 28 which is reduced with LiAlH$_4$ in THF to 9-benzyl-3,9-diazabicyclo[4.2.1]nonane 29. On reaction with compound (II) and debenzylation as described above, compound (I) is formed wherein R$^2$ is derived from compound (III) wherein m and n are each 2 and Q is hydrogen.

Compound (IV) wherein m and n are each 2 and Q is methyl may be prepared as shown in Reaction Scheme VI. Lactam 28 of Scheme V is methylated with methyl iodide and sodium hydride in DMF to form N-methyl lactam 30 which is reduced with LiAlH$_4$ in THF at reflux temperature and debenzylated as described above to form 3-methyl-3,9-diazabicyclo[4.2.1]nonane.

As described above in connection with Reaction Scheme II, compound 29 (analogous to compound 11) may be reacted with ethylchloroformate to the corresponding carbamate, the benzyl group removed by catalytic hydrogenation and the resulting compound reacted with compound (II). Compound (I) may be formed on hydrolysis, wherein R$^2$ is derived from compound (III) wherein m and n are each 2 and Q is hydrogen.

Compounds (III) and (IV) wherein m is 2, n is 3 and Q is hydrogen or methyl may be prepared as outlined in Schemes IV, V and VI and the above disclosure using as the starting material cyclooctadienone as described in J. Org. Chem., 44, 4285 (1979).

Reaction Scheme VI

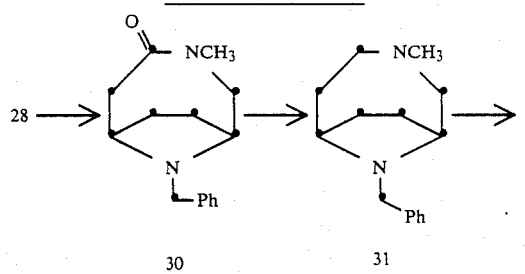

Compounds (V) wherein n is 1 and Q is hydrogen may be made as described in U.S. Pat. No. 3,947,445 and J. Org. Chem., 31, 1059 (1966). Compounds (I) wherein R$_3$ is derived from compound (V) wherein n is 1 and Q is methyl may be prepared by standard methylation with formic acid and paraformaldehyde (Eschweiler-Clark) of corresponding compounds (I) wherein Q is hydrogen.

Methods for preparing compounds (V) wherein n is 2 and Q is hydrogen or methyl are described in Heterocyclic Chem., 11, 449 (1974). The same methods may be used for preparing compounds (V) wherein n is 3 replacing adipic acid by pimelic acid as the starting material.

Compound (VI) wherein n is 1 and p is 0, 1,3-diazabicyclo[2.1.1]hexane, may be prepared from 1-benzhydryl-3-amino-azetidine 32, described in Chem. Pharm. Bull., 22, 1490 (1974), as shown in reaction Scheme VII. Diamine 33 is formed on catalytic hydrogenation e.g. with Pd on C (10%) of 32. The 1,3-bridge forms with 30% aqueous formaldehyde according to the general procedures disclosed in Aust. J. Chem., 20, 1643 (1967).

Compound (VI) wherein n and p are each one may be prepared from the known compound pyrazyl methanol 34 in Reaction Scheme VIII. Pyrazine 34 is catalytically reduced with e.g. PtO$_2$ catalyst to 2-(2-hydroxymethyl)-piperazine 35, as described in U.S. Pat. 3,281,423. Ring closure to compound VI is accomplished by chlorination with thionyl chloride and heating with aqueous sodium hydroxide.

Compound (VI) wherein n is 2 and p is 0 (1,3-diazabicyclo[2.2.1]heptane) may be prepared from commercially available N-benzylpyrrolidone 37 by reductive animation with benzylamine and sodium borohydride to 1,3-dibenzyl-3-aminopyrrolidine 38, as outlined in Reaction Scheme IX. The pyrrolidine is debenzylated by catalytic hydrogenation, as described before, and ring closure of 39 is effected with aqueous formaldehyde to compound (VI).

Reaction Scheme VII

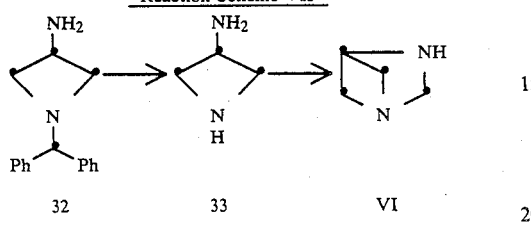

32   33   VI

Reaction Scheme VIII

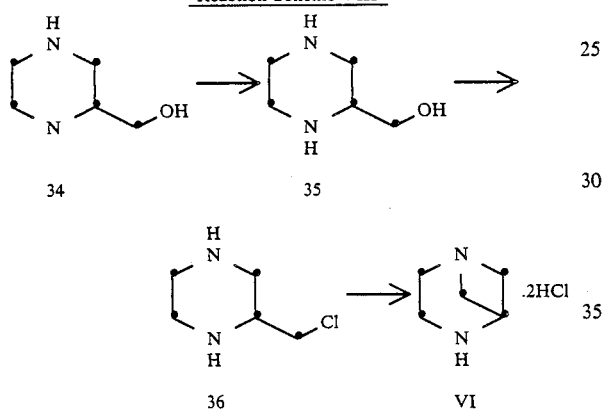

34   35

36   VI

Compound (VI) wherein n is 2 and p is 1, 1,4-diazabicyclo[3.2.1]octane is described in U.S. Pat. No. 3,954,766.

Compound (VI) wherein n is 3 and p is 0, 1,3-diazabicyclo[3.2.1]octane may be prepared from commercially available N-benzylpiperidone by the same method as shown in Reaction Scheme IX.

Compound (VI) wherein n is 3 and p is 1, 1,4-diazabicyclo[3.3.1]nonane, is prepared from known compound nipecotic acid ethyl ester 40. The secondary amine is alkylated with bromoacetic acid ethylester to 41. The diethylester is treated with potassium t-butoxide in toluene to give ketone 42 which is converted to oxime 43 as described before by treatment with hydroxylamine in aqueous sodium bicarbonate. The oxime is rearranged in hot sulfuric acid to lactam 44. Reduction with LiAlH4 leads to compound VI wherein n is 3 and p is 1.

Compound (VII) wherein n is 1, 1,3-diazabicyclo[2.2.2]octane, may be prepared from commercially available 4-amino-N-benzylpiperidine 45 as outlined in Reaction Scheme XI. The benzyl group is removed by catalytic hydrogenation e.g. with Pd/C (10%) to give 4-aminopiperidine 46. The carbon bridge is formed on treatment with aqueous formaldehyde to VII.

Compound (VII) wherein n is 2,1,4-diazabicyclo[3.2.2]nonane, is described in Org. Syn., Coll. Vol. V, 989 (1973) and Zh. Org. Khim., 1 (7), 1336 (1965).

Reaction Scheme IX

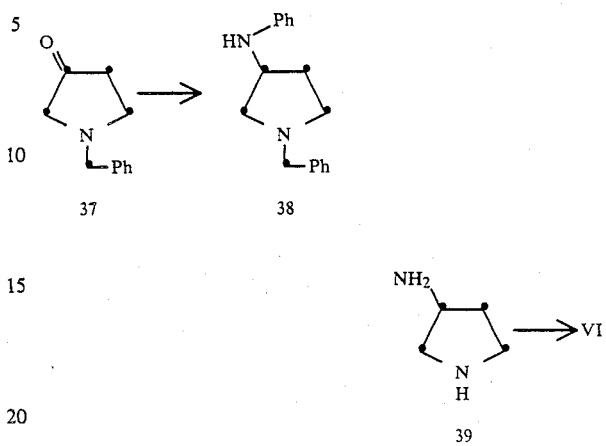

37   38

39

Reaction Scheme IX

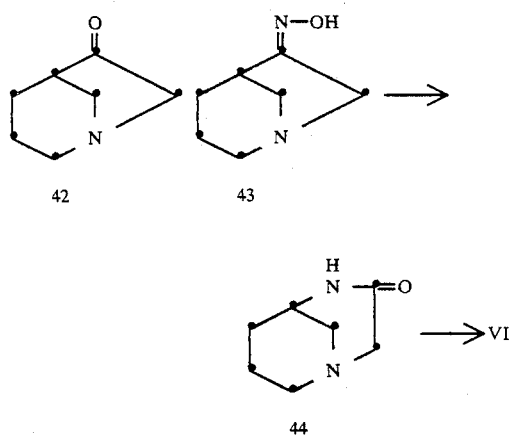

40   41

42   43

44

Reaction Scheme XI

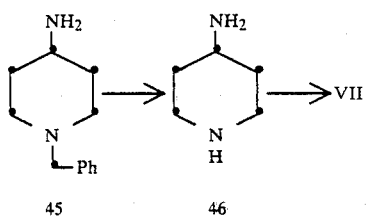

45   46

Reaction Scheme XII

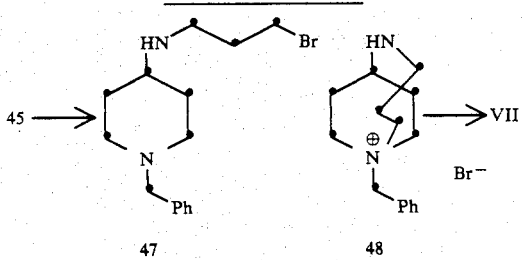

Compound (VII) wherein n is 3,1,5-diazabicyclo[4.2.2]decane, may be prepared from commercially available 4-amino-N-benzylpiperidine 45, see Reaction Scheme XII. Aminobromide 46 is formed on reductive amination of 45 with 3-bromopropionaldehyde and sodium borohydride. On heating, the quaternary ammonium bromide 48 is formed By conventional debenzylation as described before, the desired compound (VII) is formed Compounds (I) wherein Q is $(C_1-C_3)$alkyl may be prepared by substituting the required alkylamine for methylamine or the required aldehyde for formaldehyde in the above described reactions.

Compounds (I) wherein Q is $(C_1-C_6)$alkyl-carbonyl of the formula

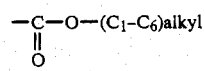

or $(C_1-C_6)$alkylcarbamoyl of the formula

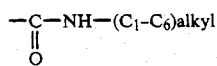

may function as prodrugs. These compounds are prepared by reacting compounds (III) to (VII) wherein Q is hydrogen with $(C_1-C_6)$alkyl chlorforomates or $(C_1-C_6)$alkylisocyanates in an inert solvent at about 0° to 100° C.

The pharmaceutically acceptable acid addition salts of compounds (I) are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, methanesulfonic, cinnamic, fumaric, phosphonic, hydrochloric, hydrobromic, hydroiodic, sulfamic, and sulfonic acid.

The pharmaceutically acceptable cationic salts of compounds (I) may be prepared by conventional methods from the corresponding acids, e.g. by reaction with about one equimolar amount of a base. These cationic salts do not increase the toxicity of the compound toward animal organisms. Examples of suitable cationic salts are those of alkali metals such as sodium or potassium, alkaline earth metals such as magnesium or calcium, and ammonium or organic amines such as diethanol amine or N-methylglucamine.

The novel compounds of formula I and the pharmaceutically acceptable acid addition salts thereof are useful in the treatment of bacterial infections of broad spectrum, particularly the treatment of grampositive bacterial strains.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1–50 mg/kg/day, advantageously 0.2–10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are abut 0.1–200 mg/kg/day, advantageously 0.5–50 mg/kg/day. While intramuscularly administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the invention.

EXAMPLE 1

1-Ethyl-6-fluoro-1,4-dihydro-7-(8-methyl-3,8-diazabicyclo[3.2.1]oct-3-yl)-4-oxo-3-quinolinecarboxylic acid (Y=ethyl; $R^1$=H; A=CH; $R^2$=a; n=2; m=1; Q=methyl)

A stirred suspension of 1-ethyl-6,7-difluoro-4-oxo-1,4-dihydro-3-quinolinecarboxylic acid (3.0 g, 11.9 mmol) and 8-methyl-3,8-diazabicyclo[3.2.1]octane dihydrochloride (4.5 g, 22.7 mmol) in 15 ml of dry pyridine under $N_2$ was treated with 1,8-diazabicyclo[5.4.0]undec-7-ene (7.0 g, 4.6 mmol). The mixture was heated to 80° C. for three hours. A solution resulted which was cooled to room temperature and poured into 50 ml of water. The aqueous solution was washed five times with 100 ml of chloroform. The combined organic layer was dried over $Na_2SO_4$, filtered and concentrated in vacuo. The resulting solid was washed with diethyl ether, dissolved in water at pH=1 with 1N hydrochloric acid and washed with chloroform. The aqueous layer was neutralized with saturated aqueous sodium bicarbonate and the product was extracted with chloroform (5×100 ml). The chloroform layer was dried over Na$_2$SO$_4$, filtered and concentrated to about 25 ml of chloroform. The pure product was precipitated as a white solid with 75 ml of diethyl ether. The solid was collected by suction filtration and washed with diethyl ether to afford 2.77 g (65% yield) of the title compound, m.p. 244°–245° C.

EXAMPLE 2

1-Ethyl-6,8-difluoro-1,4-dihydro-7-(8-methyl-3,8-diazabicyclo[3.2.1]oct-3-yl)-4-oxo-3-quinolinecarboxylic acid (Y=ethyl; R$^1$=H; A=CF; R$^2$=a; Q=methyl; n=2; m=1)

The title compound was prepared according to example 1 by reacting 1-ethyl-6,7,8-trifluoro-4-oxo-1,4-dihydroquinoline-3-carboxylic acid with 8-methyl-3,8-diazabicyclo[3.2.1]octane dihydrochloride, m.p. 215°–219° C.

EXAMPLE 3

1-Fluoroethyl-6,8-difluoro-1,4-dihydro-7-(8-methyl-3,8-diazabicyclo[3.2.1]oct-3-yl)-4-oxo-3-quinolinecarboxyic acid (Y=fluoroethyl; R$^1$=H; A=CF; R$^2$=a; n=2; m=1; Q=CH$_3$)

The title compound was prepared according to example 1 by reacting 1-fluoroethyl-6,7,8-trifluoro-oxo-1,4-dihydroquinoline-3-carboxylic acid with 8-methyl-3,8-diazabicyclo[3.2.1]octane dihydrochloride, m.p. 216°–219° C.

EXAMPLE 4

1-Methyl-6-fluoro-1,4-dihydro-7-(8-methyl-3,8-diazabicyclo[3.2.1]oct-3-yl)-4-oxo-3-quinolinecarboxylic acid Y=CH$_3$; R$^1$=H; A=CH; R$^2$=a; n=2; m=1; Q=CH$_3$)

The title compound (68% yield) was prepared according to example 1 by reacting 1-methyl-6,7-difluoro-4-oxo-1,4-dihydroquinoline-3-carboxylic acid with 8-methyl-3,8-diazabicyclo[3.2.1]octane dihydrochloride, m.p. 251°–252° C.

EXAMPLE 5

1-Vinyl-6-fluoro-1,4-dihydro-7-(8-methyl-3,8-diazabicyclo[3.2.1]oct-3-yl)-4-oxo-3-quinolinecarboxylic acid (Y=vinyl; R$^1$=H; A=CH; R$^2$=a; Q=methyl; n=2; m=1; Q=CH$_3$)

The title compound (276 mg, 66% yield) was prepared according to example 1 by reacting 1-vinyl-6,7-difluoro-4-oxo-1,4-dihydroqunoline-3-carboxylic acid (296 mg, 1.18 mmol) with 8-methyl-3,8-diazabicyclo[3.2.1]octane dihydrochloride (471 mg, 2.36 mmol), m.p. 225°–232° C. with decomposition.

EXAMPLE 6

1-p-Fluorophenyl-6-fluoro-1,4-dihydro-7-(8-methyl-3,8-diazabicyclo[3.2.1]oct-3-yl)-4-oxo-3-quinolinecarboxylic acid (Y=p-fluorophenyl; R$_1$=H; A=CH; R$_2$=a; n=2; m=1; Q=CH$_3$)

A stirred suspension of 1-p-fluorophenyl-6,7-difluoro-4-oxo-1,4-dihydro-3-quinolinecarboxylic acid (319 mg, 1.0 mmol) and 8-methyl-3,8-diazabicyclo[3.2.1]octane dihydrochloride (400 mg, 2.02 mmol) in 8 ml of dry pyridine under N$_2$ treated with 1,8-diazabicyclo[5.4.0]undec-7-ene (609 mg, 4.00 mmol). The mixture was heated to 80° C. for three hours, cooled to room temperature and poured into 25 ml of water. The aqueous layer was extracted five times with 75 ml of chloroform. The chloroform layer was dried over Na$_2$SO$_4$, filtered and concentrated in vacuo. The resulting solid was washed several times with diethyl ether and treated with 1N HCl until the pH was 1. The water-insoluble hydrochloride salt was filtered and air dried. Recrystallization from acetonitrile gave 150 mg (35% yield) of a white solid, m.p. 319°–320 (with decomposition).

EXAMPLE 8

1-Ethyl-6-fluoro-1,4-dihydro-7-(1,4-diazabicyclo[3.2.2]-non-4-yl)-4-oxo-3-quinolinecarboxylic acid (Y=ethyl; R$^1$=H; A=CH; R$^2$=e; n=2)

A stirred suspension of 1-ethyl-6,7-difluoro-4-oxo-1,4-dihydro-3-quinolinecarboxylic acid (76 mg, 0.302 mmol) and 1,4-diazabicyclo[3.2.2]nonane (95 mg, 0.754 mmol) in 3 ml of dry pyridine under N$_2$ was heated to 90° C. for 18 hours. The mixture was cooled to room temperature and diluted with 50 ml of water. The aqueous solution was extracted two times with 50 ml of chloroform. The combined organic layers were then washed twice with water, dried over Na$_2$SO$_4$, filtered and concentrated in vacuo. The solid was triturated several times with diethylether and filtered to give (27 mg, 25% yield) of a pale yellow solid, m.p. 223°–225° C.

EXAMPLE 8

1-Ethyl-6-fluoro-1,4-dihydro-7-(9-methyl3,9-diazabicyclo[4.2.1]non-3-yl)-4-oxo-3-quinolinecarboxylic acid (Y=ethyl; R$^1$=H; A=CH; R$^2$=a; n=m=2; Q=CH$_3$)

A suspension of 1-ethyl-6,7-difluoro-1,4-dihydro-oxo-3-quinolinecarboxylic acid (578 mg, 2.28 mmol) in 20 ml of dry pyridine under N$_2$ was treated with 9-methyl-3,9-diazabicyclo[4.2.1]nonane (800 mg, 5.71 mmol). The mixture was heated to 90° C. for three hours, cooled to room temperature and poured into 200 ml of water. The aqueous solution was extracted three times with 100 ml of chloroform. The combined chloroform extracts were washed twice with 150 ml of 1N hydrochloric acid. The aqueous extracts were washed once with 300 ml of chloroform and then the pH was adjusted to 6.8 with 6N NaOH. The aqueous solution was extracted three times with 200 ml of chloroform. The final chloroform extracts were dried over Na$_2$SO$_4$, filtered and concentrated to give a pale yellow solid. This material was washed with diethylether and ethylacetate in a volume ratio of 1:1 to give 453 mg (53% yield) of a pale yellow solid, m.p. 187°–188° C.

EXAMPLE 9

1-Ethyl-6,8-difluoro-1,4-dihydro-7-(1,4-diazabicyclo[3.2.2]non-4-yl)-4-oxo-3-quinolinecarboxylic acid (Y=ethyl; $R^1$=H; A=CF; $R^2$=d; n=2; p=1; Q=H)

A. 3-oxo-1,4-diazabicyclo[3.2.2]nonane

Quinuclidone HCl (200 g, 1.24 moles) was dissolved in concentrated sulfuric acid (500 ml) and chilled to 0°–5° C. in a very large ice-water bath. $NaN_3$ (200 g, 3.07 moles) was added in small portions over 2 hours. The resulting mixture was stirred at 0° C. for 4 hours. The reaction mixture was then slowly and carefully diluted with 1 liter of water and slowly quenched with a solution of sodium hydroxide (900 g, 22.5 moles) in 1.5 liters of water. After the quench, the pH of the reaction mixture was approximately 13.5. The resulting sodium sulfate was filtered and then washed with 2 liters of chloroform. The aqueous supernatant was extracted with three times 2 l of chloroform. The combined extracts were dried with magnesium sulfate and concentrated to give 94.9 g of a solid residue. This residue was chromatographed (2.0 kg $SiO_2$; 9:1 chloroform:methanol) to give 13.59 g of the title compound as white crystals, m.p. 210°–211° C., yield 7.8%.

In addition 42.9 g of a byproduct identified as 2-(3,4-dehydropiperidin-1-yl)acetamide was isolated as white plates, m.p. 121°–122° C., yield 24.7%.

B. 1,4-diazabicyclo[3.2.2]nonane

Lithium aluminum hydride (2.0 g, 51.4 mmoles) was slurried in 250 ml of dry tetrahydrofuran and 3-oxo-1,4-diazabicyclo[3.2.2]nonane (3.6 g, 25.7 mmoles) was added carefully as a solid in one portion at room temperature. The resulting mixture was then heated to a gentle reflux for 20 hours. The reaction was cooled to room tempeature and quenched by slow addition of 2.5 ml water. The salts were filtered and washed several times with diethyl ether totaling 1.0 l. These washings and the supernatant were combined, dried over magnesium sulfate and concentrated to give 2.09 g (64.5%) of the title compound as a pale yellow oil.

NMR ($^{13}$C; 63 MHz, $CDCl_3$): 59.11, 47.97, 46.67, 43.67, 29.43.

C. 6,7,8-Trifluoro-1-ethyl-1,4-dihydro-4-oxo-3-quinolinecarboxylic acid (271 mg, 1.0 mmol) was dissolved in 5 ml of dry pyridine and heated to 90° C. 1,4-Diazabicyclo[3.2.2]nonane (315 mg, 2.5 mmoles) in 1 ml of dry pyridine was added and the resulting mixture was heated at 90° C. for 2.5 hours. The solution was then cooled to 10° C. resulting in the formation of a precipitate which was filtered and washed several times with ethyl acetate and dried under vacuum to afford 103 mg (27%) of the title compound as a cream colored solid with m.p. 261°–263° C.

EXAMPLE 10

1-(2-Fluoroethyl)-6-fluoro-1,4-dihydro-7(1,4-diazabicyclo[3.2.2]-non-4-yl)-4-oxo-3-quinolinecarboxylic acid.

(Y=2-fluoroethyl; $R^1$=H; A=CH; $R^2$=d; n=2; p=1; Q=H)

The title compound was prepared in 50.1% yield according to example 9 by reacting 6,7-difluoro-1-(2-fluoroethyl)-1,4-dihydro-4-oxo-3-quinoline carboxylic acid with 1,4-diazabicyclo[3.2.2]nonane, m.p. 256°–258° C.

EXAMPLE 11

1-Vinyl-6-fluoro-1,4-dihydro-7-(1,4-diazabicyclo[3.2.2]-non-4-yl)-4-oxo-3-quinolinecarboxylic acid.

(Y=vinyl; $R^1$=H; A=CH; $R^2$=d; n=2; p=1; Q=H)

The title compound was prepared in 49.6% yield according to example 9 by reacting 6,7-difluoro-1-vinyl-1,4-dihydro-4-oxo-3-quinoline carboxylic acid with 1,4-diazabicyclo[3.2.2]nonane, m.p. 255°–257° C.

EXAMPLE 12

1-(4-Fluorophenyl)-6-fluoro-1,4-dihydro-7-(1,4-diazabicyclo[3.2.2]non-4-yl)-4-oxo-3-quinolinecarboxylic acid.

(Y=4-fluorophenyl; $R^1$=H; A=CH; $R^2$=d; n=2; p=1; Q=H)

The title compound was prepared in 68% yield according to example 9 by reacting 6,7-difluoro-1-(4-fluorophenyl)-1,4-dihydro-4-oxo-3-quinolinecarboxylic acid with 1,4-diazabicyclo[3.2.2]nonane, m.p. 320° C.

NMR: ($CDCl_3$ and $DMSOd_6$, 250 MHz): 8.60 (1H, s); 7.98 (1H, d, J=13 Hz); 7.54 (2H, m); 7.41 (2H, m); 6.28 (1H, d, J=7Hz); 3.89 (1H, m); 3.26 (2H, t); 2.9–3.15 (6H, m); 1.95–2.10 (2H, m); 1.75–1.90 (2H, m).

EXAMPLE 13

1-Methylamino-6-fluoro-1,4-dihydro-7-(1,4-diazabicyclo-[3.2.2]non-4-yl)-4-oxo-3-quinoline carboxylic acid (Y=methylamino; $R^1$=H; A=CH; $R^2$=d; n=2; p=1; Q=H)

The title compound was prepared in 73% yield according to example 9 by reacting 6,7-difluoro-1-methylamino-1,4-dihydro-4-oxo-3-quinoline carboxylic acid with 1,4-diazabicyclo[3.2.2]nonane, m.p. 245°–247° C.

EXAMPLE 14

10-(1,4-Diazabicyclo[3.2.2]non-4-yl)-9-fluoro-3-methyl-7-oxo-2,3-dihydro-(7H)-pyrido(1,2,3-de)-1,4-benzoxazine-6-carboxylic acid (A—Y=CH—O—$CH_2$—C($CH_3$)H; $R^1$=H; $R^2$=d; n=2; p=1; Q=H)

9,10-Difluoro-3-methyl-7-oxo-2,3-dihydro-(7H)-pyrido-(1,2,3-de)-1,4-benzoxazine-6-carboxylic acid (281 mg, 1.0 mmol) was dissolved in 5 ml DMSO and heated to 120° C. 1,4-Diazabicyclo[3.2.2]nonane (315 mg, 2.5 mmoles) in 1 ml dry pyridine was added and the resulting mixture was heated at 120° C. for 4.5 hours. The solution was then cooled to room temperature and poured in 250 ml water. The aqueous mixture was extracted 3 times with 250 ml chloroform. The combined chloroform extracts were further extracted 3 times with 1.0 N HCl (250 ml). The aqueous acidic extracts were combined and neutralized to a pH of 7.0 with 6N NaOH, and then extracted 3 times with 250 ml chloroform. The combined chloroform extracts were dried over sodium sulfate and stripped of solvent to give asolid residue that was slurried in ethyl acetate, filtered, washed with ethyl acetate, and dried to give the title compound (55 mg, 14% yield) as a pale yellow solid, m.p. 230°–232° C.

EXAMPLE 15

1-Vinyl-6-fluoro-7-(9-methyl-3,9diazabicyclo[4.2.1]-non-3-yl)-1,4-dihydro-4-oxo-3-quinoline carboxylic acid (Y=vinyl; $R^1$=H; A=CH; $R^2$=a; m=n=2; Q=$CH_3$)

A. 9-Methyl-4-oxo-3,9-diazabicyclo[4.2.1]nonane

Tropinone (5.0 g, 35.97 mmoles) was dissolved in a mixture of concentrated sulfuric acid (20 ml) and chloroform (50 ml) and chilled to 0°–5° C. in an efficient ice-water bath. NaN3 (5.8 g, 89.9 mmoles) was added in small portions over 15 minutes. The resulting mixture was stirred at 0° C. for 1 hour. After this time the reaction mixture was diluted carefully with 50 ml water and sufficient solid $K_2CO_3$ was added to raise the pH of the mixture to 9.5. Then 250 ml chloroform was added and the entire mixture was filtered. The layers were separated and the aqueous layer was extracted with an additional 250 ml of chloroform. The combined chloroform extracts were dried over magnesium sulfate and concentrated to give a solid residue that was recrystallized from diethyl ether to give 3.36 g (60.6%) of the title compound A as colorless needles, m.p. 78°–80° C.

B. 7-Methyl-3,9-diazabicyclo[4.2.1]nonane

Lithium aluminum hydride (1.56 g, 40 mmoles) was slurried in 75 ml dry tetrahydrofuran and 9-methyl-4-oxo-3,9-diazabicyclo[4.2.1]nonane (3.36 g, 21.8 mmoles) dissolved in 20 ml tetrahydrofuran was added dropwise at room temperature. The resulting mixture was heated to gentle reflux for 28 hours, then cooled to room temperature and carefully quenched by the slow additions of 3 ml water. 500 ml of diethyl ether was added and the mixture was filtered of solids, dried over magnesium sulfate, and concentrated to give 2.45 g (80.3%) of the title compound B as a colorless oil.

NMR (250 MHz, $DMSOd_6$): 4.0–4.2 (2H, m); 3.45–3.6 (2H, m); 3.2–3.35 (2H, m); 2.84 (3H, s); 1.9–2.5 (6H, m).

C. The title comound was prepared in 44.7% yield according to example 8 by reacting 6,7-difluoro-1-vinyl-1,4-dihydro-4-oxo-3-quinoline-carboxylic acid with 9-methyl-3,9-diazabicyclo[4.2.1]nonane, m.p. 214°–215° C.

EXAMPLE 16

1-Methyl-6-fluoro-7-(9-methyl-3,9-diazabicyclo[4.2.1]-non-3-yl)-1,4-dihydro -4-oxo-3-quinoline carboxylic acid (Y=methyl; $R^1$=H; A=CH; $R^2$=a; m=n=2; Q=$CH_3$)

The title compound was prepared in 8.5% yield according to example 8 by reacting 6,7-difluoro-1-methyl-1,4-dihydro-4-oxo-3-quinoline carboxylic acid with 9-methyl-3,9-diazabicyclo[4.2.1]nonane, m.p. 220°–222° C.

EXAMPLE 17

1-(2-Fluoroethyl)-6-fluoro-1,4-dihydro-7(9-methyl-3,9-diazabicyclo[4.2.1]non-3-yl)-4-oxo-3-quinoline carboxylic acid (Y=2-fluoroethyl; $R^1$=H; A=CH; $R^2$=a; m=n=2; Q=$CH_3$)

The title compound was prepared in 13% yield according to Example 8 by reacting 6,7-difluoro-1(2-fluoroethyl)-1,4-dihydro-4-oxo-3-quinolinecarboxylic acid with 9-methyl-3,9-diazabicyclo[4.2.1]nonane, m.p. 202°–203° C.

EXAMPLE 18

1-(2-Fluoroethyl)-6,8-difluoro-1,4-dihydro-7-(1,4-diazabicyclo[3.2.2]non-4-yl)-4-oxo-3-quinoline carboxylic acid ($R^1$=H; Y=2-fluoroethyl; A=CF, $R^2$=d; n=2; p=1)

The title compound was prepared in 13.3% yield according to example 9 by reacting 6,7,8-trifluoro-1-(2-fluoroethyl)-1,4-dihydro-4-oxo-3-quinoline carboyxlic acid with 1,4-diazabicyclo[3,2,2]nonane, m.p. 238–239° C.

EXAMPLE 19

1-Cyclopropyl-6-fluoro-7-(1,4-diazabicyclo[3.2.2]-non-4-yl)-1,4-dihydro-4-oxo-3-quinoline carboxylic acid $R^1$=H; Y=cyclopropyl; A=CH; $R^2$=d; n=2; p=1)

The title compound was prepared in 68.4% yield according to example 9 by reacting 6,7-difluoro-1-cyclopropyl-1,4-dihydro-4-oxo-3-quinoline carboxylic acid with 1,4-diazabicyclo[3,2,2]nonane, m.p. 296°–297° C.

EXAMPLE 20

1-Ethyl-6-fluoro-7-(9-benzyl-3,9-diazabicyclo[4.2.1]-non-3-yl)1,4-dihydro-4-oxo-3-quinoline carboxylic acid ($R^1$=H; Y=ethyl; A=CH; $R^2$=a; m=n=2; Q=benzyl)

A. The title compound was prepared according to example 8 in 63% yield by reacting 6,7-difluoro-1-ethyl-1,4-dihydro-4-oxo-3-quinoline carboxylic acid with 9-benzyl-3,9-diazabicyclo[4,2,1]nonane, m.p. 218°–220° C.

1-Ethyl-6-fluoro-7-(3,9-diazabicyclo[4.2.1]non-3-yl)-1,4-dihydro-4-oxo-3-quinoline carboxylic acid ($R^1$=H; Y=ethyl; A=CH; $R^2$=a; m=n=2; Q=H)

B. 7-(9-benzyl-3,9-diazabicyclo[4,2,1]non-3-yl)--fluoro-1-ethyl-1,4-dihydro-4-oxo-3-quinoline carboxylic acid (963 mg, 2.15 mmoles) was dissolved in 125 ml of methanol that was previously saturated with HCl. To this solution was added 1.25 g of 10% Pd/C and the mixture was treated with an atmosphere of 45 psi hydrogen on a Parr hydrogenation apparatus at 60° C. for 4.5 hours. The mixture was then cooled to room temperature and filtered of catalyst through a celite pad. The filtrate was stripped to dryness, taken up in water (50 ml) and the pH was adjusted to 7.0 with saturated sodium bicarbonate. This aqueous layer was extracted with three times 200 ml chloroform which was dried over sodium sulfate and evaporated to give a solid residue. This residue was taken up in a small amount of chloroform and ether from which crystallized an off-white material that was filtered and dried to give 149 mg (19.3%) of the title compound, m.p. 147°–150° C.

EXAMPLE 21

1-Ethyl-6-fluoro-7-(3-methyl-3,9-diazabicyclo[4.2.1]-non-9-yl)-1,4-dihydro-4-oxo-3-quinoline carboxylic acid ($R^1$=H; Y=ethyl; A=CH; $R^2$=b; n=2; Q=$CH_3$)

The title compound was prepared in low ( 5%) yield according to example 1 by reacting 6,7-difluoro-1-ethyl- 1,4-dihydro-4-oxo-3-quinoline carboxylic acid with 3-methyl-3,9-diazabicyclo[4.2.1]nonane, m.p.=234°–236° C.

EXAMPLE 22

1-Ethyl-6-fluoro-1,4-dihydro-7-(9-methyl-3,9-diazabicyclo[3.3.1]non-3-yl)-4-oxo-3-quinoline carboxylic acid ($R^1$=H; Y=ethyl; A=CH; $R^2$=a; m=1; n=3; Q=$CH_3$)

The title compound (172 mg, 47% yield) was prepared according to example 1 by reacting 1-ethyl-6,7-difluoro-4-oxo-1,4-dihydroquinoline-3-carboxyic acid (250 mg, 0.99 mmol) with 9-methyl-3,9-diazabicyclo[3.3.1]nonane (526 mg, 2.47 mmole) dihydrochloride, m.p. 180°–182° C.

EXAMPLE 23

10-(8-Methyl-3,8-diazabicyclo[3.2.1]oct-3-yl)-9-fluoro-3-methyl-7-oxo-2,3-dihydro-(7H)-pyrido-(1,2,3-de)-1,4-benzoxazine-6-carboxylic acid ($R^1$=H; A—Y=C—O—$CH_2$—C($CH_3$)H; $R^2$=a; m=1; n=2; Q=methyl)

9,10-Difluoro-3-methyl-7-oxo-2,3-dihydro-(7H)pyrido(1,2,3-de)-1,4-benzoxazine-6-carboxylic acid (425 mg, 1.51 mmol), 8-methyl-3,8-diazabicyclo[3.2.1]octane dihydrochloride (425 mg, 2.14 mmol) and 1,8diazabicyclo[5.4.0]undec-7-ene (672 mg, 4.41 mmol) were dissolved in 8.0 ml of dry DMSO. The reaction mixture was heated to 80° C. for 29 hours, cooled to room temperature and poured into 100 ml of water. The product was then extracted with chloroform, dried over sodium sulfate, filtered and evaporated to a small volume.

Ether was then added to precipitate beige crystals which were purified by acid-base treatment to give 125 mg (21% yield) of a cream colored solid, m.p. 248°–252° C.

EXAMPLE 24

1-(2-Fluoroethyl)-6-fluoro-1,4-dihydro-7-(8-methyl-3,8-diazabicyclo[3.2.1]oct-3-yl)-4-oxo-3-quinoline carboxylic acid ($R^1$=H; Y=2-fluoroethyl; A=CH; $R^2$=a; m=1; n=2; Q=methyl)

The title compound (288 mg, 52% yield) was prepared according to example 1 by reacting 1-ethyl-6,7-difluoro-4-oxo-1,4-dihydroquinoline-3-carboxylic acid (363 mg, 1.34 mmol) with 8-methyl-3,8-diazabicyclo[3.2.1]octane dihydrochloride (400 mg, 2.0 mmol) in 1,8-diazabicyclo[5.4.0]undec-7-ene (610 mg, 4.01 mmol) and pyridine (4.0 ml) at 80° C. for 3 hours, m.p. 270°–273° C. (HCl salt).

EXAMPLE 25

1-Ethyl-6-fluoro-1,4-dihydro-7-{(1S,4S) 5-benzyl-2,5-diazabicyclo[2.2.1]hept-2-yl)}4-oxo-3-quinoline carboxylic acid ($R^1$=H; Y=ethyl; A=CH; $R^2$=c; n=1; Q=benzyl)

A. The title compound (70 mg, 33% yield) was prepared according to example 1 by reacting 1-ethyl-6,7-difluoro-4-oxo-1,4-dihydro-3-quinoline caboxylic acid (126 mg, 0.5 mmol) with (1S, 4S) 5-benzyl-2,5-diazabicyclo[2.2.1]heptane dihydroiodide (444 mg, 1.0 mmol) in 1,8-diazabicyclo[4.5.0]undec-7-ene (305 mg, 2.0 mmol) in pyridine (5 ml) at 80° C. for 2 hours, m.p. 208°–209° C.

1-Ethyl-6-fluoro-1,4-dihydro-7-{(1S,4S) 2,5-diazabicyclo[2.2.1]hept-2-yl)}-4-oxo-3-quinoline carboxylic acid ($R^1$=H; Y=ethyl; A=CH; $R^2$=c; n=1; Q=H)

B. A stirred suspension of 1-ethyl-6,7-difluoro-4-oxo-1,4-dihydro-3-quinoline carboxylic acid (506 mg, 2.0 mmol) and (1S:4S)-2,5-diazabicyclo[2.2.1]heptane dihydrochloride (680 mg, 4.0 mmol) in 20 ml of dry pyridine was treated with 1,8-diazabicyclo[5.4.0]-undec-7-ene(1.2 g, 8.0 mmol). The mixture was heated to 80° C. for 3 hours, cooled to room temperature and poured into water. The aqueous phase was extracted with chloroform (3 times 50 ml). The product precipitated from the aqueous layer on standing and was collected by suction filtration, air dried, and recrystallized from hot acetonitrile to give (90 mg, 14% yield) of an off-white solid, m.p. 283°–285° C.

EXAMPLE 26

1-Cyclopropyl-6-fluoro-1,4-dihydro-7-{(1S:4S) 2,5-diazabicyclo[2.2.1]hept-2-yl)}-4-oxo-3-quinoline carboxylic acid ($R^1$=H; Y=cyclopropyl; A=CH; $R^2$=c; n=1; Q=H)

The title compound (167 mg, 63%) was prepared by reacting 6,7-difluoro-1-cyclopropyl-1,4-dihydro-4-oxo-3-quinoline carboxylic acid (207 mg, 0.78 mmol) with (1S:4S)2,5-diazabicyclo[2.2.1]heptane dihydrochloride (249 mg, 1.46 mmol) in 1,8-diazabicyclo[5.4.0]undec-7-ene (450 mg, 2.96 mmol) and pyridine (3 ml) at 80° C. for 2 hours, m.p. 301°–302° C. w/decomp (recrystallized from chloroform:methanol, 1:1 (v/v)).

EXAMPLE 27

1-Cyclopropyl-6-fluoro-1,4-dihydro-7-(8-methyl-3,8-diazabicyclo[3.2.1]oct-3-yl)-4-oxo-3-quinoline carboxylic acid ($R^1$=H; Y=cyclopropyl; A=CH; $R^2$=a; m=1; n=2; Q=methyl)

A stirred suspension of 6,7-difluoro-1-cyclopropyl-4-oxo-1,4-dihydro-3-quinoline carboxylic acid (1.5 g, 5.66 mmol) and 8-methyl-3,8-diazabicyclo[3.2.1]octane dihydrochloride (1.45 g, 7.32 mmol) in 10.0 ml of pyridine was treated with 1,8-diazabicyclo[5.4.0]undec-7-ene (2.26 g, 14.9 mmol). The reaction mixture was heated to 80° C. for 4 hours, cooled to room temperature and poured into 250 ml of chloroform. The chloroform layer was washed with water (twice 200 ml), dried over sodium sulfate, filtered and concentrated in vacuo. The crude off white solid was dissolved in 1N hydrochloride with warming and this solution was washed with chloroform/methanol (9:1 v/v). The aqueous solution as then basified with saturated aqueous sodium bicarbonate and extracted with chloroform (three times 200 ml). The chloroform layer was dried with sodium sulfate, filtered, concentrated in vacuo, and washed with diethyl ether to give 1.80 g (86% yield) of an off white solid, m.p. 278°–279° C. with decomposition.

We claim:

1. A compound of the formula

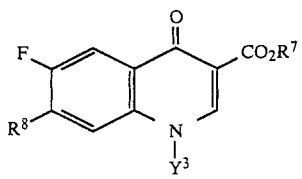

or a pharmaceutically acceptable acid addition salt thereof, wherein $R^7$ is hydrogen, a pharmaceutically acceptable cation, or $(C_1-C_6)$alkyl;

$Y^3$ is cyclopropyl; and $R^8$ is 8-methyl-3,8-diazabicyclo[3.2.1]oct-3-yl, (1S, 4S)-2,5-diazabicyclo[2.2.1]hept-2-yl, or (1S, 4S)-5-methyl-2,5-diazabicyclo[2.2.1]hept-2-yl.

2. A compound according to claim 1, wherein $R^7$ is hydrogen.

3. A compound according to claim 1, wherein said compound is 1-cyclopropyl-6-fluoro-1,4-dihydro-7-(8-methyl-3,8-diazabicyclo[3.2.1]oct-3-yl)-4-oxo-3-quinoline carboxylic acid.

4. A compound according to claim 1, wherein said compound is 1-cyclopropyl-6-fluoro-1,4-dihydro-7-[(1S,4S)-2,5-diazabicyclo[2.2.1]hept-2-yl]-4-oxo-3-quinoline carboxylic acid.

5. A compound according to claim 1, wherein said compound is 1-cyclopropyl-6-fluoro-1,4-dihydro-7-[(1S,4S)-5-methyl-2,5-diazabicyclo-[2.2.1]hept-2-yl]-4-oxo-3-quinoline carboxylic acid.

6. A compound according to claim 1 wherein said compound is 1-cyclopropyl-6-fluoro-1,4-dihydro-7-(8-methyl-3,8-diaza-bicyclo[3.2.1]oct-3-yl)-4-oxo-3-quinoline carboxylic acid hydrochloride salt.

7. A compound according to claim 1, wherein said compound is 1-cyclopropyl-6-fluoro-1,4-dihydro-7-(8-methyl-3,8-diazabicyclo[3.2.1]oct-3-yl)-4-oxo-3-quinoline carboxylic acid methanesulfonate salt.

8. An antibacterial composition comprising a compound according to claim 1 in an amount sufficient for treatment of a bacterial disease, and a pharmaceutically acceptable carrier.

9. A composition according to claim 8 wherein $R^7$ is hydrogen.

10. A composition according to claim 8 wherein said compound is 1-cyclopropyl-6-fluoro-1,4-dihydro-7-[(1S,4S)-2,5-diazabicyclo[2.2.1]hept-2-yl]-4-oxo-3-quinoline carboxylic acid.

11. A composition according to claim 8 wherein said compound is 1-cyclopropyl-6-fluoro-1,4-dihydro-7-[(1S,4S)-5-methyl-2,5-diazabicyclo[2.2.1]hept-2-yl]-4-oxo-3-quinoline carboxylic acid.

12. A composition according to claim 8 wherein said compound is 1-cyclopropyl-6-fluoro-1,4-dihydro-7-[(1S,4S)-5-methyl-2,5-diazabicyclo[2.2.1]hept-2-yl]-4-oxo-3-quinoline carboxylic acid methanesulfonate salt.

13. A composition according to claim 8 wherein $R^7$ is $(C_1-C_6)$alkyl.

14. A composition according to claim 8 wherein $R^7$ is methyl or ethyl.

15. A method of treating a host affected by a bacterial infection which comprises administering to said host an antibacterially effective amount of a compound according to claim 1.

* * * * *